US009179888B2

(12) United States Patent
Ji et al.

(10) Patent No.: US 9,179,888 B2
(45) Date of Patent: Nov. 10, 2015

(54) SYSTEM AND METHOD FOR PROVIDING PATIENT REGISTRATION WITHOUT FIDUCIALS (75) Inventors: Songbai Ji, Lebanon, NH (US); David W. Roberts, Lyme, NH (US); Alex Hartov, Enfield, NH (US); Keith D. Paulsen, Hanover, NH (US)

(73) Assignee: Dartmouth College, Hanover, NH (US)

( * ) Notice: Subject to any disclaimer, the term of this patent is extended or adjusted under 35 U.S.C. 154(b) by 86 days.

(21) Appl. No.: 13/392,173

(22) PCT Filed: Aug. 27, 2010

(86) PCT No.: PCT/US2010/046961
§ 371 (c)(1),
(2), (4) Date: May 7, 2012

(87) PCT Pub. No.: WO2011/025943
PCT Pub. Date: Mar. 3, 2011

(65) Prior Publication Data
US 2012/0215093 A1    Aug. 23, 2012

Related U.S. Application Data (60) Provisional application No. 61/237,825, filed on Aug. 28, 2009.

(51) Int. Cl.
*A61B 5/05*    (2006.01)
*A61B 8/00*    (2006.01)
(Continued)

(52) U.S. Cl.
CPC . *A61B 8/00* (2013.01); *A61B 5/064* (2013.01); *A61B 6/5247* (2013.01);
(Continued)

(58) Field of Classification Search
CPC ............. A61B 19/5244; A61B 2017/00725; A61B 2019/5236; A61B 2019/5255; A61B 2019/5276; A61B 2019/5289; A61B 5/064; A61B 6/501; A61B 6/5247; A61B 8/00; A61B 8/0816; A61B 8/4245; A61B 8/5238
USPC ................................................. 600/407, 437
See application file for complete search history.

(56) References Cited

U.S. PATENT DOCUMENTS

2002/0128550 A1    9/2002  Van Den Brink et al.
2002/0158873 A1*  10/2002  Williamson ................. 345/427
(Continued)

OTHER PUBLICATIONS

Thevenaz P., Unser M., "Optimization of mutual information for multiresolution image registration," Image Processing, IEEE Transactions on , vol. 9, No. 12, pp. 2083-2099, Dec. 2000.*
(Continued)

*Primary Examiner* — Jonathan Cwern
*Assistant Examiner* — Amelie R Gillman
(74) *Attorney, Agent, or Firm* — Peter A. Nieves; Sheehan Phinney Bass + Green, PA (57) ABSTRACT A method for providing patient registration without fiducials comprises the steps of: spatially placing an ultrasound image of a patient randomly at different starting positions relative to a preoperative image; creating an independent registration corresponding to each different starting positions, by optimizing a spatial transformation between the preoperative image and the ultrasound image to provide a first batch of registrations; executing a second registration to fine-tune the alignment between the preoperative image and the ultrasound image; and concatenating the spatial transformation to obtain spatial transformation between the patient in an operating room and a corresponding preoperative image.

18 Claims, 5 Drawing Sheets

(51) Int. Cl.
*A61B 5/06* (2006.01)
*A61B 8/08* (2006.01)
*A61B 19/00* (2006.01)
*G06T 7/00* (2006.01)
*A61B 6/00* (2006.01)
*A61B 17/00* (2006.01)

(52) U.S. Cl.
CPC ............ *A61B 8/0816* (2013.01); *A61B 8/4245* (2013.01); *A61B 8/5238* (2013.01); *A61B 19/5244* (2013.01); *G06T 7/0024* (2013.01); *A61B 6/501* (2013.01); *A61B 2017/00725* (2013.01); *A61B 2019/5236* (2013.01); *A61B 2019/5255* (2013.01); *A61B 2019/5276* (2013.01); *A61B 2019/5289* (2013.01)

(56) References Cited

U.S. PATENT DOCUMENTS

| | | | |
|---|---|---|---|
| 2004/0059217 | A1 | 3/2004 | Kessman et al. |
| 2004/0092815 | A1 | 5/2004 | Schweikard et al. |
| 2004/0138560 | A1 | 7/2004 | Paladini |
| 2005/0013471 | A1* | 1/2005 | Snoeren et al. ............... 382/131 |
| 2005/0228251 | A1* | 10/2005 | Grabb et al. .................. 600/407 |
| 2007/0015991 | A1 | 1/2007 | Fu et al. |
| 2008/0095421 | A1 | 4/2008 | Sun et al. |
| 2008/0123927 | A1* | 5/2008 | Miga et al. .................... 382/131 |
| 2008/0269604 | A1* | 10/2008 | Boctor et al. ................. 600/437 |
| 2009/0080746 | A1* | 3/2009 | Xu et al. ....................... 382/131 |
| 2009/0097722 | A1* | 4/2009 | Dekel et al. ................... 382/128 |
| 2009/0097778 | A1 | 4/2009 | Washburn et al. |
| 2009/0148019 | A1* | 6/2009 | Hamada et al. ............... 382/131 |
| 2009/0297006 | A1* | 12/2009 | Suri et al. ..................... 382/131 |
| 2009/0306507 | A1 | 12/2009 | Hyun et al. |
| 2009/0326363 | A1 | 12/2009 | Li et al. |

OTHER PUBLICATIONS

Ji, Songbai; Roberts, David W.; Hartov, Alex; Paulsen, Keith D.; Combining Multiple True 3D Ultrasound Image Volumes through Re-registration and Rasterization; Med Image Comput Comput Assist Interv. Author manuscript; available in PMC Jun. 14, 2010.
Dekomien, Claudia; Hold, Stephanie; Hensel, Karin; Schmidz, Georg; Winter, Susanne; Registration of Intraoperative 3D ultrasound with preoperative MRI Data for Navigated Surgery—first results at the knee; Proceedings of Computer Assisted Orthopaedic Surgery (CAOS), pp. 133-136, 2007.
Dhibi, M.; Solaiman, B.; Puentes, J.; Validation of Calibration by Spatial Registration between US and MRI Scans: Applications to Carotid of Bifurcation; Information and Communication Technologies: From Theory to Applications, 2009. ICTTA 2008, vol. 7, Issue 11, Apr. 2008; pp. 1-4.
Gobbi, David G.; Comeau, Roch M., Peters, Terry M.; Ultrasound/MRI Overlay with Warping for Neurosurgery; Medical Imaging Computing and Computer-Assisted Intervention; Copyright 2000, Springer Berlin/ Heidelberg, pp. 29-53.
Gobbi, David G.; Comeau, Roch M., Lee, Belinda, K.H.; Peters, Terry M.; Correlation of Pre-Operative MRI and Intra-Operative MRI and Intra-Operative 3D Ultrasound to Measure Brain Tissue Shift; Proc. SPIE 3982, Medical Imaging 2000: Ultrasonic Imaging and Signal Processing, 77 (Apr. 12, 2000).
Roche, Alexis; Pennec, Xavier; Malandain, Gregoire; Ayache, Nicholas; Rigid Registration of 3-D Ultrasound With MR Images: A New Approach to Combining Intensity and Gradient Information; IEEE Transactions on Medical Imaging, vol. 20, No. 10, Oct. 2001, p. 1038-1049.
Winter, S.; Hansen, D.; Dekomien, C.; Pechlivanis,I.; Engelhardt, M.; Ermert, H.; Schmeider, K.; Ultrasound-Based Registration of Preoperative CT or MRI Data for Navigation in Brain Surgery; Tagungsband der 6. Jahrestagung der Deutschen Gesellschaft fur Computer- und Robotergiestuzte Chirurgie; Oct. 13, 2007, p. 79-81.
Shams, R.; Sadeighi, P.; Kennedy, R.A.; Gradient Intensity: A New Mutual Information-Based Registration Method; Computer Vision and Pattern Recognition, Jun. 2007, p. 1-8.
Porter, D.C.; Rubens, D.J.; Strang, J.G.; Smith, J.; Totterman, S.; Parker, K.J.; Three Dimensional Registration and Fusion of Ultrasound and MRI Using Major Vessels as Fiducial Markers; IEEE Transactions on Medical Imaging, vol. 20, Issue 4, Apr. 2001, pp. 354-359.
Masahiro Sakakibara, MD, PhD, Takeshi Nagashima, MD, PhD, Takafumi Sangai, MD, PhD, Rikiya Nakamura, MD, Hiroshi Fujimoto, MD, Manabu Arai, MD, Toshiki Kazama, MD, PhD, Hideyuki Hashimoto, MD, PhD, Yukio Nakatani, MD, PhD, Masaru Miyazaki, MD, PhD; Breast-Conserving Surgery Using Projectionand Reproduction Techniques of Surgical-Position Breast MRI in Patients with Ductal Carcinoma In Situ of the Breast; 2008 by the American College of Surgeons; Published by Elsevier Inc.
Songbai Ji, Alex Hartov, David Roberts, Keith Paulsen; "Mutual-Information-Based Patient Registration Using Intraoperative Ultrasound Guided Neurosurgery", Medical Physics 35(1), pp. 4612-4624 (2008).

* cited by examiner

SYSTEM AND METHOD FOR PROVIDING PATIENT REGISTRATION WITHOUT FIDUCIALS

CROSS-REFERENCE TO RELATED APPLICATIONS

This application claims priority to U.S. Provisional Application entitled, "PATIENT REGISTRATION WITHOUT FIDUCIALS," having Ser. No. 61/237,825, filed Aug. 28, 2009 and PCT Application entitled "PATIENT REGISTRATION WITHOUT FIDUCIALS,", which is entirely incorporated herein by reference.

GOVERNMENT STATEMENT

This invention was made with government support under Contract Number RO1 EB002082-11 awarded by NIH. The government has certain rights in the invention.

BACKGROUND OF THE INVENTION

Patient registration is routinely performed in image-guided surgery to establish a required spatial transformation between anatomies of interest and the corresponding preoperative images. The accuracy of an image-guidance system directly depends on the accuracy of the patient registration based on which image navigation is provided.

Currently, patient registration is performed using fiducials either affixed to skin or implanted in bone. Bone-implanted fiducials provide the most accurate registration, but are invasive to the patient and result in discomfort to the patient. By contrast, skin-affixed fiducials are less accurate, but they are noninvasive and are therefore, more commonly employed. Unfortunately, fiducials have to remain on the skin or in the bone of the patient from the time the preoperative images are acquired until patient registration is finished, which is usually hours.

Fiducial-based registration requires manual identification of fiducials in the operating room as well as in the image space (although some commercial systems are able to identify fiducial locations automatically in the image space), which accounts for a significant amount of operating room time. As an example it typically takes around ten minutes or more to perform patient registration, and even more when patient registration has to be repeated. In addition, accurate identification of fiducials also requires sufficient training.

Thus, a heretofore unaddressed need exists in the industry to address the aforementioned deficiencies and inadequacies.

SUMMARY OF THE INVENTION

Embodiments of the present invention provide a system and method for providing a completely automatic, image-based patient registration that does not rely on fiducial markers placed on the patient prior to acquiring preoperative images before surgery. The invented patient registration technique can, therefore, be employed to provide surgical guidance in cases where no fiducials are available.

The method for providing patient registration without fiducials comprises the steps of: spatially placing an ultrasound image of a patient randomly at different starting positions relative to a preoperative image; creating an independent registration corresponding to each different starting positions, by optimizing a spatial transformation between the preoperative image and the ultrasound image to provide a first batch of registrations; executing a second registration to fine-tune the alignment between the preoperative image and the ultrasound image; and concatenating the spatial transformation to obtain spatial transformation between the patient in an operating room and a corresponding preoperative image.

In addition, a general system of the present invention contains a memory and a processor configured by the memory to perform the steps of: spatially placing an ultrasound image of a patient randomly at different starting positions relative to a preoperative image; creating an independent registration corresponding to each different starting positions, by optimizing a spatial transformation between the preoperative image and the ultrasound image to provide a first batch of registrations; executing a second registration to fine-tune the alignment between the preoperative image and the ultrasound image; and concatenating the spatial transformation to obtain spatial transformation between the patient in an operating room and a corresponding preoperative image.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

The present system and method provides an automatic fiducial-less registration that does not require user guidance. The following provides an example of use of the present system and method in the framework of image-guided neurosurgery, although it should be noted that the present invention is not limited to use in image-guided neurosurgery.

The present system and method establishes a spatial transformation between ultrasounds and magnetic resonance images. Specifically, the present description is with regard to establishing a spatial transformation between volumetric true 3D intra-operative ultrasound (iUS) and preoperative images (including magnetic resonance (pMR) and CT, although the former is much more widely used to provide unparrelled delineation of soft tissues in the brain) of a patient. It should be noted that pMR is used in the present description for exemplary purposes only and is not intended to be a limitation to the present invention.

Figure 1:
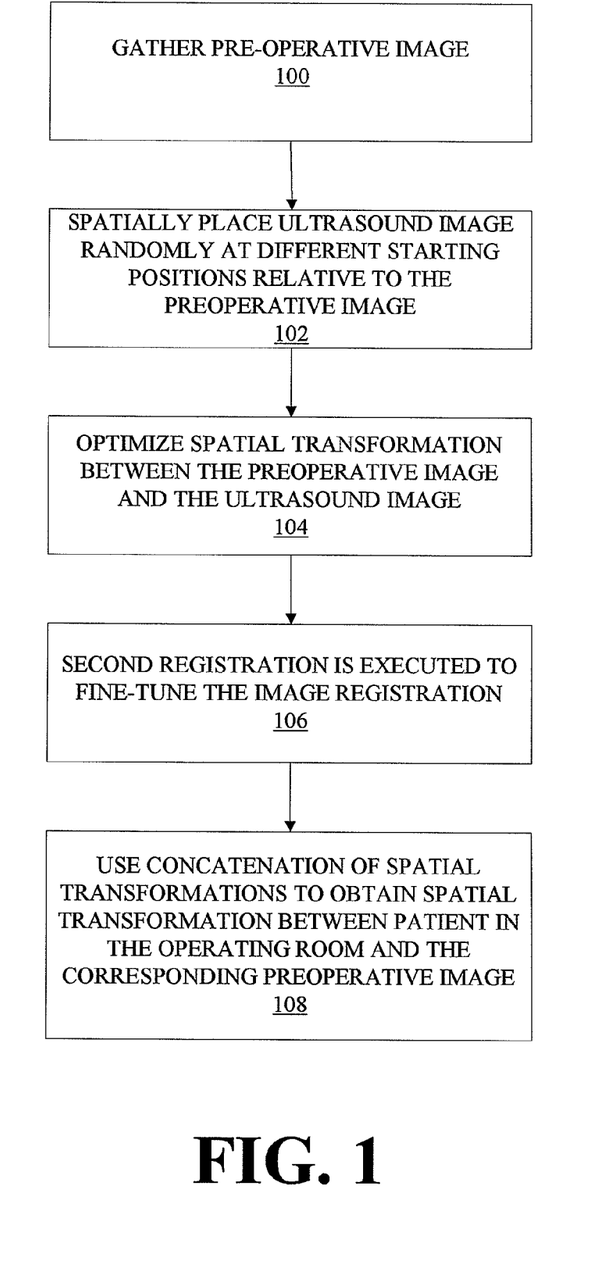
FIG. 1 is a flowchart further illustrating the steps involved in providing patient registration without fiducials.

FIG. 1 is a flow chart further illustrating the steps involved in providing patient registration without fiducials. As is known by those having ordinary skill in the art, a registration is a transformation that can be applied to two images so that they align with each other. It should be noted that any process descriptions or blocks in flow charts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

As shown by block 100, a preoperative image is taken before entering the operating room. The preoperative image is usually taken hours before the surgery or the night before the surgery in a conventional imaging suite.

As shown by block 102, an ultrasound image of a patient is spatially placed randomly at different starting positions relative to the preoperative image. It should be noted that the ultrasound image could be taken at any time, when a patient registration is desired.

As shown by block 104, an independent registration, corresponding to each different starting position, is created by optimizing the spatial transformation between the preoperative image and the ultrasound image, as is explained below in detail with regard to FIG. 2. This is referred to as a first batch of registrations, thereby signifying that multiple independent registrations are involved.

Figure 2:
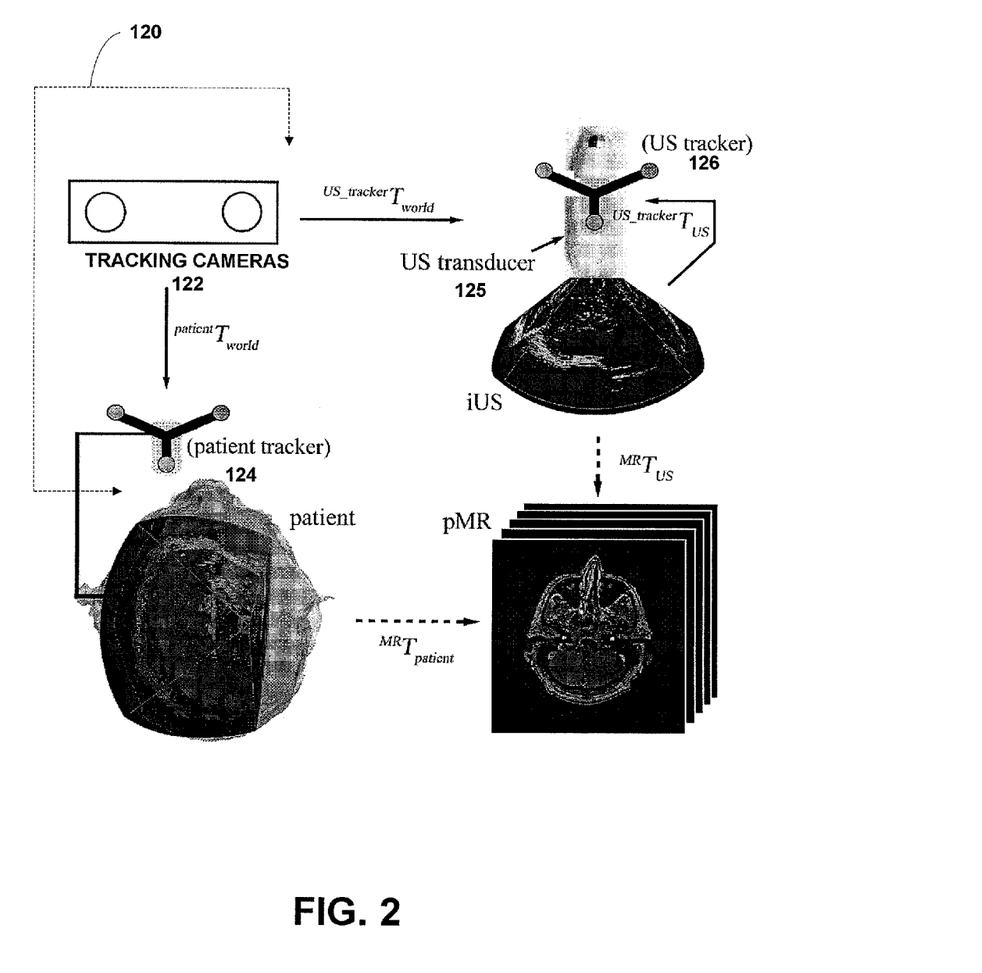
FIG. 2 illustrates coordinate systems involved in image transformations.

FIG. 2 demonstrates that the first batch of registrations result in a transformation close to the "true" registration, and can be used as a new starting point for a second registration, as explained below. Not all solutions are used as a new starting point. In fact, it is preferred that only one solution be used as a new starting point for the second registration. As is further described herein, one determines which solution to use based on the corresponding image similarity measure, i.e., the solution that provides the maximum value of image similarity measure will be used subsequently as the new starting point for the second registration. A "true" registration is described in further detail below. Determining the optimal spatial location of the ultrasound image is performed by the computer of FIG. 5.

Figure 5:
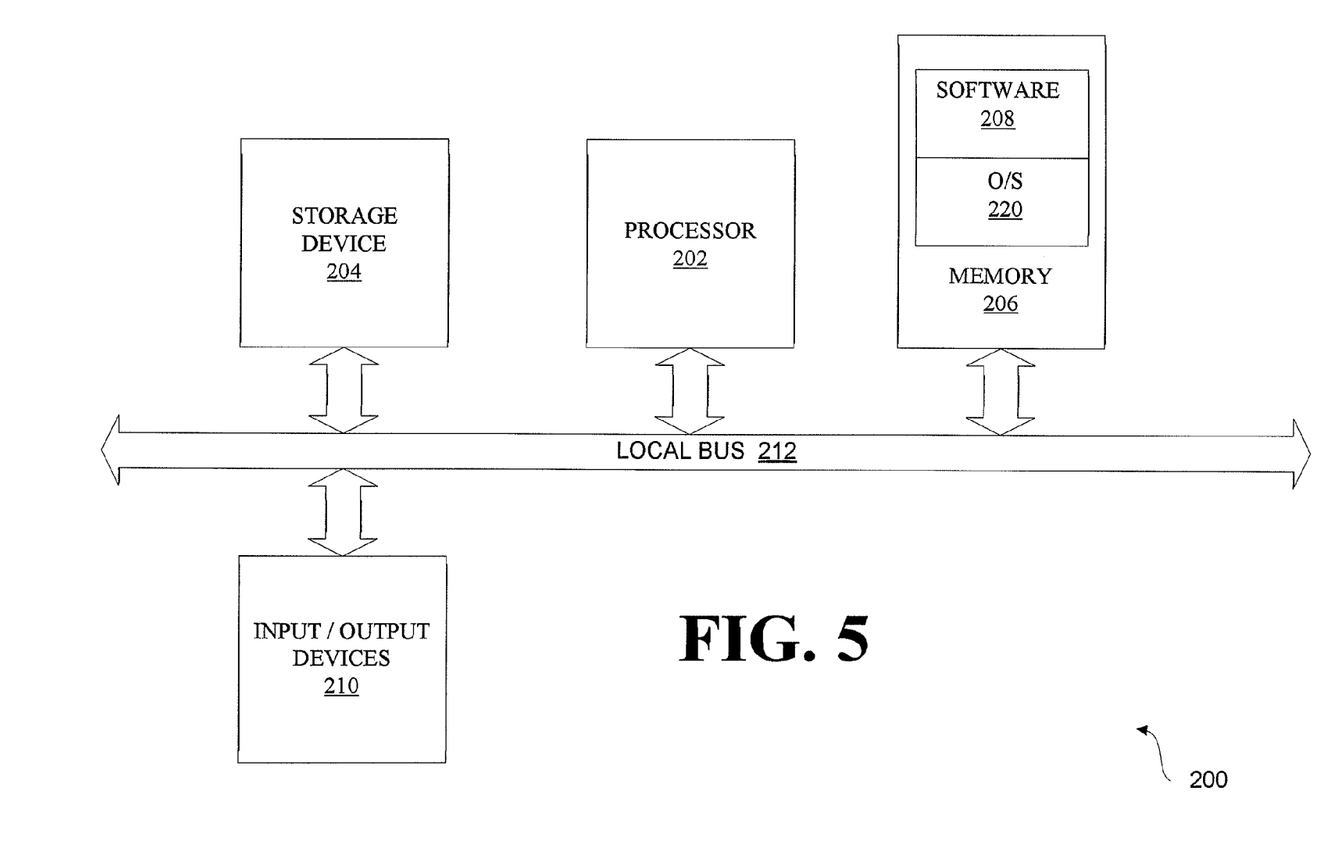
FIG. 5 is a schematic diagram illustrating an example of a system for executing functionality of the present invention.

It should be noted that spatially placing and creating independent registration may be performed by any device containing a processor and a memory, such as, for example, a general purpose computer, an example of which is illustrated by FIG. 5.

The reason for randomly generating multiple different starting positions of the ultrasound image relative to pMR is because image-based registrations, as an example, maximizing the mutual information between US and pMR, may not converge to a correct transformation when the initial starting point is too far away from the "true" registration (outside of what is referred to as a "capture range"). The "true" registration refers to the "ground-truth", correct registration, which is unknown. The current process is provided to establish a registration that is as close to the "true" registration as possible. It should be noted that a registration, as referred to in the term "true" registration, is a spatial transformation to align two objects or images. A registration is different from an image.

By randomly generating a sufficient number of initial starting points, some of the converged transformations will be close enough to the "true" registration. From these converged transformations, the converged transformation that has the maximum mutual information will be used as a new starting position in a second registration, which is further described below.

Since the purpose for the first batch of registrations is to generate a good starting point for use in the second registration, it is desirable to execute fast, however it is not necessary that these registrations be accurate. Therefore, the pMR and US images are preprocessed so that binary images (where image intensities are either zero or one) are used in the first batch of registrations. It is to be noted that binary images lose information, and hence, registration results may not be accurate. By contrast, preprocessed grayscale (where image intensities are ranged from 0 to 255 for 8-bit grayscale) pMR and US images are used in the second registration to generate accurate registration results. It is to be noted that grayscale images preserve information and result in more accurate registration results.

There is another reason why binary images are used in the first batch of registrations, specifically, a larger "capture range" is obtained with these binary images, which effectively reduces the number of random initial starting points required to achieve a good registration result in the first step of registration.

Using the present optimization method, an initial guess of the solution is provided (in the present registration problem, an initial guess of solution is the same as an initial registration). If the initial guess is sufficiently close to the true solution (in the present case, the "true registration"), more than likely the optimization process will yield a solution that is very close to the true solution. When the initial guess is farther away from the true solution, the likelihood of the optimization process to generate a correct solution will become less and less. A "capture range" is a measure to gauge how far away the initial guess can be relative to the "true" solution, that the optimization method is still able to generate a solution that is close to the true solution most of the time.

As shown by block 106 of FIG. 1, a second registration is executed by the computer to fine-tune the alignment between the preoperative image and the ultrasound image. The second registration is performed by maximizing the mutual information between the ultrasound image and the preoperative image, which is to use the mutual information as an objective function with respect to the spatial transformation between ultrasound images and preoperative images. An optimization method is used to maximize the objective function. Once the objective function (i.e., mutual information) is maximized, the resulting spatial transformation will be used to align the two images. Both registrations are performed in the operating room, although the present invention is not limited to both registrations being performed in the operating room.

As shown by block 108, concatenation of spatial transformations is used by the computer to obtain spatial transformation between the patient in the operating room and the corresponding preoperative image.

As shown by FIG. 2, the phrase "patient registration" refers to finding a rigid body transformation between preoperative images (e.g., pMR in FIG. 2) and the patient in the operating room (e.g., patient in FIG. 2): $^{MR}T_{patient}$ in FIG. 2. This transformation is to transform from the patient to the corresponding preoperative MR images. It should be noted that the preoperative images are not limited to MR images.

FIG. 2 illustrates coordinate systems involved in image transformations. In FIG. 2, solid arrows indicate transformations determined from calibration, while dashed arrows indicate transformations determined from registration. A transformation reversing the arrow direction is obtained by matrix inversion.

With a tracking system 120 (such as, for example, but not limited to, an optical tracking system as illustrated in FIG. 2) and transformation concatenation, the following equation one (Eq. 1) establishes the relationship between the various transformations:

$$^{MR}T_{patient} = inv(^{patient}T_{world}) \times {}^{US\_tracker}T_{world} \times inv(^{US\_tracker}T_{US}) \times {}^{MR}T_{US} \quad \text{Eq. 1}$$

As illustrated by equation one above, there are multiple transformations required in order to compute the transformation on the left of equation one, as is explained in further detail herein. The first two transformations on the right of equation one need to be provided by the tracking system 120, while the third transformation is determined by calibrating an ultrasound transducer 125, while the last transformation on the right is what the present two-step registration approach is trying to find. Once all transformations are determined, the transformation on the left of equation one can be computed, which is the "patient registration" sought in accordance with the present invention.

As illustrated by FIG. 2, the tracking system 120 may include a series of tracking cameras 122 and a series of trackers 124, wherein each tracker 124 represents a coordinate of a specific object, such as, for example, the head of a patient. It should be noted that in the present description, a tracker that is rigidly connected to a patient is also referred to as a patient tracker. In addition, as shown by FIG. 2, an ultrasound tracker 126 is rigidly attached to the ultrasound transducer 125.

In the above equation one, the left term is the transformation pursued, namely, the spatial transformation from the patient in the operating room to the corresponding preoperative MR images. On the right, $^{patient}T_{world}$ and $^{US\_tracker}T_{world}$ are known from the tracking system 120, and they represent the spatial transformation from the tracking system 120 to the patient and spatial transformation from the tracking system 120 to the ultrasound (US) transducer 125, respectively.

Specifically, both the patient tracker 124 and US tracker 126 are continuously tracked by the tracking system 120 and their position and orientation are explicitly given by the tracking system, while $^{US\_tracker}T_{US}$ is obtained from US transducer 125 calibration, which is fixed once calibration is performed. Note that transducer calibration is performed in the laboratory before hand, which does not interfere with registration in the operating room. The way to track the patient and ultrasound transducer 125 is to rigidly attach a tracker with them, and track the corresponding trackers. Take the patient for example: the patient head is rigidly fixed to the surgical table, and is also rigidly attached with a tracker (referred to herein as a "patient tracker" to differentiate from other trackers). The tracking system 120 is able to track the spatial position and orientation of the patient tracker 124, and because the patient tracker 124 is rigidly fixed to the head, the tracking system 120 effectively tracks the spatial position and orientation of the head.

An example of an optical tracking system is the Polaris optical tracking system, created by Northern Digital Inc., of Ontario, Canada.

The last term of equation one, $^{MR}T_{US}$, is the transformation of interest. This transformation is obtained following the two-step image-based registration process. When this transformation ($^{MR}T_{US}$) is obtained, then "patient registration," which establishes the spatial transformation between the preoperative MR images of the patient and the ultrasound image of the patient, is computed following equation one. The resulting patient registration (i.e., $^{MR}T_{patient}$) is all that is needed to provide neuronavigation in the operating room. It is also the same transformation that fiducial-based registrations are used to compute.

To summarize the abovementioned, the present method utilizes a tracked and calibrated ultrasound probe, and patient registration is achieved by using a two-step registration process between ultrasound and preoperative images of the anatomy. A first batch of registrations is intended to execute fast and to efficiently locate a transformation in the vicinity of the ground-truth or true registration. It should be noted that image registration is the same as locating a transformation. A second registration is based on the best result obtained from the previous registrations, and is intended to execute slower but with much improved accuracy. Both registrations are performed when an ultrasound (US) image is acquired, anytime before or during surgery as long as the US image can be acquired. The latter condition says that if the US transducer can acquire brain images with the skull intact (e.g., a transcranial transducer), then one can perform the present registration process, including the first and second registration of the present invention, prior to surgery starting. If otherwise an ultrasound image has to be acquired after craniotomy, then the registration has to be performed when the skull is removed at the surgical site.

A series of coarse registrations is performed to establish an initial starting point close to the "true" registration to allow refinement in the second registration. This is the first batch of registrations. The first batch of registrations are executed immediately after the US image is acquired. It should be noted that a "true" registration is a correct registration. Image-based registration that maximizes the mutual information between two image sets does not necessarily converge to a "true" registration. When the initial starting point is too far away from the true registration (i.e., too much mis-alignment between the two image sets before the registration), the maximization process may converge to an incorrect transformation. Although the mutual information is maximized to a local maximum, the resulting spatial transformation does not correctly align the two image sets. The fundamental reason for the possibility of incorrect registration result is because the mutual information as a function with respect to the 6 degrees-of-freedom (DOFs; 3 translational and 3 rotational variables) is a complex mathematical function, which has multiple local maxima.

For exemplary purposes, suppose the true registration corresponds to the 6 DOFs of [0 0 0 0 0 0], then if we choose a starting point of [1 2 −1 −2 1 −2] and run the registration (i.e., maximizing the mutual information), we may well converge to the true registration of [0 0 0 0 0 0]. However, suppose that we choose a starting point of [100 −100 100 −100 100 −100], then we may well not converge to the true registration because the starting point is too far away, and the converged result would be incorrect. Since we do not know the "true" registration in advance, we have to probe in space to hopefully generate a starting point close to the true registration, which converges to, e.g., [0.5, −0.5 0.5 −0.5 0.3 −0.2]. The resulting transformation is then used as a new starting point for the second registration to refine the transformation. As an example, for image-guided neurosurgery, a volumetric 3D iUS image that captures the parenchymal surface contralateral to the craniotomy (and the scan-head probe tip) before dural opening can be selected for registration purposes. Angular ranges of the 3D iUS image will be selected to sample the parenchymal surface maximally, which is important to reduce the likelihood of incorrect registration due to feature symmetry.

Figure 3:
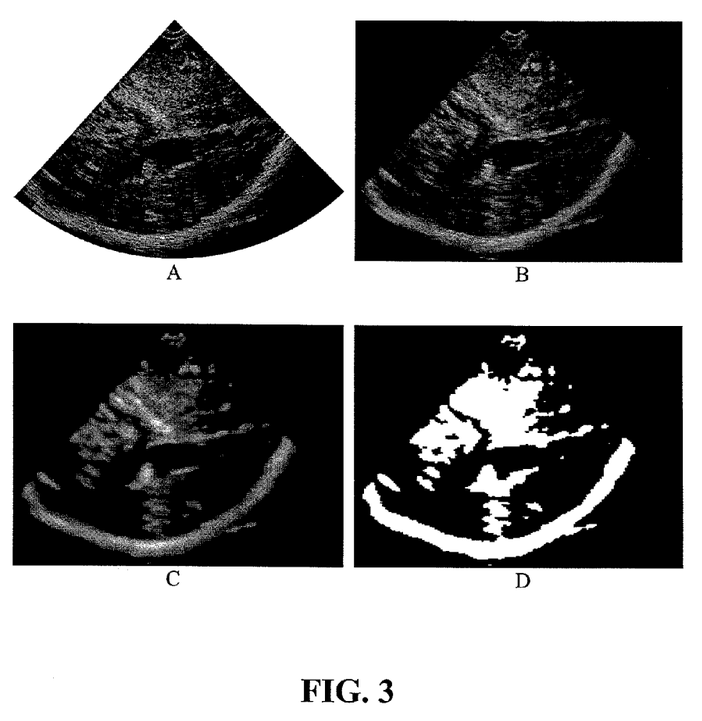
FIG. 3A is an illustration, in 2D, of pre-processing of a 3D intraoperative ultrasound (iUS) image that captures the parenchymal surface.
FIG. 3B is a rasterized 3D iUS image corresponding to the illustration of FIG. 3A.
FIG. 3C is a Gaussian smoothed and thresholded image corresponding to the illustration of FIG. 3A.
FIG. 3D is a binary image that corresponds to the illustration of FIG. 3A.

Image pre-processing (rasterization, Gaussian smoothing, thresholding, and morphology operations) is performed to generate a binary image volume that mainly highlights the parenchymal surface. FIG. 3A is a two-dimensional illustration of pre-processing of a 3D iUS image that captures the parenchymal surface. FIG. 3B provides a rasterized 3D iUS image, while FIG. 3C illustrates a Gaussian smoothed and thresholded image, and FIG. 3D illustrates a corresponding binary image.

Figure 4:
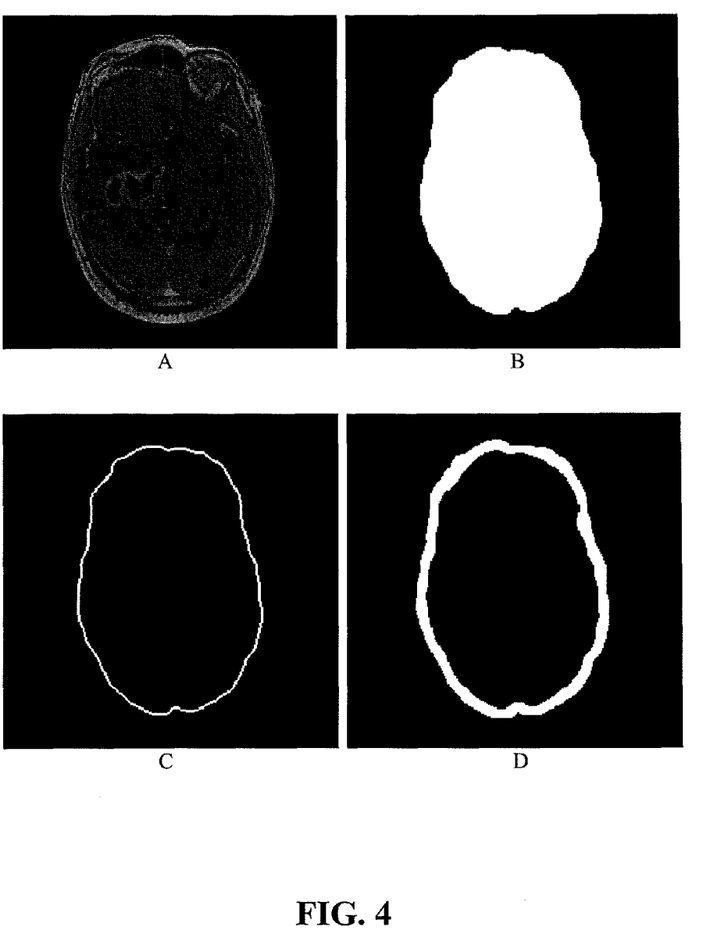
FIG. 4A is an illustration of a representative two-dimensional preoperative MR (pMR) image.
FIG. 4B is an illustration of image preprocessing on a pMR image volume, where the image is a segmented brain.
FIG. 4C is an illustration of a binary image after thresholding the gradient image, which corresponds to the illustration of FIG. 4A.
FIG. 4D is an illustration of a dilated binary image, which corresponds to the illustration of FIG. 4A.

Similarly, pMR images are also pre-processed (segmentation of the brain using an automatic, well-established level set technique and morphology operations) to highlight the same region and to emulate its appearance in the corresponding binary iUS image volume. FIGS. 4A-4D are illustrations of image preprocessing on a pMR image volume, where FIG. 4A is a representative 2D pMR image, FIG. 4B illustrates a segmented brain, FIG. 4C is a binary image after thresholding the gradient image, and FIG. 4D illustrates a dilated binary image.

These binary image volumes are used in the coarse registrations where a number of probe-tip locations and orientations with respect to the pMR image volume are generated to establish multiple initial starting points. As an example, because the iUS probe-tip is known to be in the vicinity of the brain surface, one can randomly choose the surface nodal positions of the triangulated brain surface generated from segmented pMR as potential probe-tip locations (e.g., N=10).

For each probe-tip location, a number of possible scan-head orientations (e.g., N=10) will also be randomly generated while maintaining its central axis to be along the corresponding surface nodal normal. Effectively, this strategy reduces the degrees of freedom (DOFs) of the initial starting point to two, instead of 6 DOFs in space.

An independent registration between the pre-processed binary 3D iUS and pMR image volumes is launched for each initial starting point (e.g., N=10×10=100), and their converged image similarity measure (e.g., mutual information (MI)) is recorded. Due to the "binary" nature of the two volumes, the maximum MI corresponds to a spatial transformation that results in the largest overlapping area of the brain surface region between iUS and pMR. In addition, the translational and rotational capture ranges of the "intra-modality" registration are expected to be large enough for some of the registrations to converge close to the "true" registration. The converged transformation(s) will be used as the initial starting point(s) for the second refinement registration using the grayscale images (as opposed to binary volumes in coarse registrations) to account for internal features when calculating MI, similarly to image-based registration described above (e.g., same pre-processing steps are used). The overall computational cost scales linearly with the number of random initial starting points when the coarse registrations are performed sequentially.

In accordance with one exemplary embodiment of the invention, multi-core clusters are utilized to perform multiple registrations simultaneously with the sole purpose of speeding up the computation. Optimal numbers of random positions and orientations of the iUS probe-tip can be explored to yield a successful registration with minimum computational cost. In addition, if use of this completely automatic approach is still too inefficient, one can limit the number of trials further by avoiding regions of improbable scan-head location, such as, but not limited to, the brainstem.

In accordance with another exemplary embodiment of the invention, prior knowledge of the location of craniotomy is incorporated to constrain the location of scan-head, while still randomly generating multiple scan-head orientations, with minimal manual intervention facilitated by a dedicated graphical user interface (GUI).

By incorporating prior knowledge, such as, but not limited to, approximate position of the ultrasound probe relative to preoperative images based on craniotomy and/or tumor site, the computation cost associated with the above-mentioned process is reduced to less than five minutes.

In summary, the present system and method eliminates the need for fiducials or any manual intervention, while achieving an inter-modality image registration, and can be executed completely automatically with satisfying and accurate patient registration results.

While the abovementioned patient registration method is provided in the framework of image-guided neurosurgery, the present system and method is capable of being implemented in other image-guidance systems as long as registration between ultrasound and preoperative images is feasible. Non-limited examples include, but are not limited to, image-guided surgery of the liver and of the abdomen. Of course, other examples exist for implementation of the present system and method in other image-guidance systems.

As previously mentioned, the present system for executing the functionality described in detail above may be a computer, an example of which is illustrated by FIG. 5. The system 200 contains a processor 202, a storage device 204, a memory 206 having software 208 stored therein that defines the above-mentioned functionality, input and output (I/O) devices 210 (or peripherals), and a local bus, or local interface 212 allowing for communication within the system 200. The local interface 212 can be, for example but not limited to, one or more buses or other wired or wireless connections, as is known in the art. The local interface 212 may have additional elements, which are omitted for simplicity, such as controllers, buffers (caches), drivers, repeaters, and receivers, to enable communications. Further, the local interface 212 may include address, control, and/or data connections to enable appropriate communications among the aforementioned components.

The processor 202 is a hardware device for executing software, particularly that stored in the memory 206. The processor 202 can be any custom made or commercially available processor, a central processing unit (CPU), an auxiliary processor among several processors associated with the present system 200, a semiconductor based microprocessor (in the form of a microchip or chip set), a macroprocessor, or generally any device for executing software instructions.

The memory 206 can include any one or combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory 206 may incorporate electronic, magnetic, optical, and/or other types of storage media. Note that the memory 206 can have a distributed architecture, where various components are situated remote from one another, but can be accessed by the processor 202

The software 208 defines functionality performed by the system 200, in accordance with the present invention. The software 208 in the memory 206 may include one or more separate programs, each of which contains an ordered listing of executable instructions for implementing logical functions of the system 200, as described below. The memory 206 may contain an operating system (O/S) 220. The operating system essentially controls the execution of programs within the system 200 and provides scheduling, input-output control, file and data management, memory management, and communication control and related services.

The I/O devices 210 may include input devices, for example but not limited to, a keyboard, mouse, scanner, microphone, etc. Furthermore, the I/O devices 210 may also include output devices, for example but not limited to, a printer, display, etc. Finally, the I/O devices 210 may further include devices that communicate via both inputs and outputs, for instance but not limited to, a modulator/demodulator (modem; for accessing another device, system, or network), a radio frequency (RF) or other transceiver, a telephonic interface, a bridge, a router, or other device.

When the system 200 is in operation, the processor 202 is configured to execute the software 208 stored within the memory 206, to communicate data to and from the memory 206, and to generally control operations of the system 200 pursuant to the software 208, as explained above.

It should be emphasized that the above-described embodiments of the present invention are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

We claim:

1. A method for providing a patient registration without fiducials or manual intervention, by a device containing a processor and a memory, comprising the steps of:
    generating a binary preoperative image from a grayscale preoperative image of a patient;
    generating a binary intraoperative image from a grayscale intraoperative image of the patient;
    generating multiple different random starting registration positions of the binary intraoperative image relative to the binary preoperative image;
    performing a first batch of registrations of the binary intraoperative image with the binary preoperative image, wherein the first batch of registrations comprises multiple registrations each corresponding to one random starting registration position of the multiple different random starting registration positions;
    converging information from the first batch of registrations to generate a new starting registration position;
    executing a second registration between the grayscale preoperative image and the grayscale intraoperative image from the new starting registration position; and
    computing the patient registration directly from the second registration,
    wherein the new starting registration position is the only starting registration position for the second registration, and the first batch of registrations and the second registration do not involve user guidance.

2. The method of claim 1, wherein the step of executing the second registration further comprises the step of maximizing mutual information between the grayscale intraoperative image and the grayscale preoperative image so as to use the mutual information as an objective function with respect to the second registration between the grayscale intraoperative image and the grayscale preoperative image.

3. The method of claim 1, wherein the grayscale preoperative image is a magnetic resonance image.

4. The method of claim 1, wherein generating a binary intraoperative image from a grayscale intraoperative image further comprises highlighting a parenchymal surface.

5. The method of claim 4, wherein highlighting a parenchymal surface further comprises image preprocessing by one or more of the group consisting of rasterization, Gaussian smoothing, thresholding, and morphology operations.

6. The method of claim 4, wherein generating a binary preoperative image from a grayscale preoperative image further comprises highlighting the parenchymal surface.

7. The method of claim 1, wherein the grayscale intraoperative image is an ultrasound image.

8. The method of claim 1, further comprising the step of generating multiple orientations of a source of the intraoperative binary image for each of the different random starting registration positions of the binary intraoperative image relative to the binary preoperative image.

9. The method of claim 1, wherein computing the patient registration further comprises the step of combining the second registration with a patient tracker transformation provided by a patient tracking system and a transducer tracker transformation provided by a transducer used to provide the grayscale intraoperative image.

10. A system for providing a patient registration without fiducials or manual intervention, comprising:
    a memory; and
    a processor configured by the memory to perform the steps of:
        generating a binary preoperative image from a grayscale preoperative image of a patient;
        generating a binary intraoperative image from a grayscale intraoperative image of the patient;
        generating multiple different random starting registration positions of the binary intraoperative image relative to the binary preoperative image;
        performing a first batch of registrations of the binary intraoperative image with the binary preoperative image, wherein the first batch of registrations comprises multiple registrations each corresponding to one random starting registration position of the multiple different random starting registration positions;
        converging information from the first batch of registrations to generate a new starting registration position;
        executing a second registration between the grayscale preoperative image and the grayscale intraoperative image from the new starting registration position; and
        computing the patient registration directly from the second registration,
        wherein the new starting registration position is the only starting registration position for the second registration, and the first batch of registrations and the second registration do not involve user guidance.

11. The system of claim 10, wherein the step of executing the second registration further comprises the step of maximizing mutual information between the grayscale intraoperative image and the grayscale preoperative image so as to use the mutual information as an objective function with respect to the second registration between the intraoperative image and the preoperative image.

12. The system of claim 10, wherein the grayscale preoperative image is a magnetic resonance image.

13. The system of claim 10, wherein generating a binary intraoperative image from a grayscale intraoperative image further comprises highlighting a parenchymal surface.

14. The system of claim 13, wherein highlighting a parenchymal surface further comprises image preprocessing by one or more of the group consisting of rasterization, Gaussian smoothing, thresholding, and morphology operations.

15. The system of claim 13, wherein generating a binary preoperative image from a grayscale preoperative image further comprises highlighting the parenchymal surface.

16. The system of claim 10, wherein the grayscale intraoperative image is an ultrasound image.

17. The system of claim 10, further comprising the step of generating multiple orientations of a source of the intraoperative binary image for each of the different random starting registration positions of the binary intraoperative image relative to the binary preoperative image.

18. The system of claim 10, wherein computing the patient registration further comprises the step of combining the second registration with a patient tracker transformation provided by a patient tracking system and a transducer tracker transformation provided by a transducer used to provide the grayscale intraoperative image.

* * * * *